United States Patent [19]
Platt et al.

[11] Patent Number: 4,912,025
[45] Date of Patent: Mar. 27, 1990

[54] PHOTOGRAPHIC RECORDING MATERIAL FOR ACCELERATED DEVELOPMENT

[75] Inventors: Norma B. Platt, Ontario; Drake M. Michno; David A. Steele, both of Webster; David T. Southby, Rochester, all of N.Y.

[73] Assignee: Eastman Kodak Company, Rochester, N.Y.

[21] Appl. No.: 209,614

[22] Filed: Jun. 21, 1988

[51] Int. Cl.$^4$ .................. G03C 7/32; G03C 7/34; G03C 7/36
[52] U.S. Cl. .................. 430/544; 430/380; 430/543; 430/549; 430/959
[58] Field of Search ............... 430/380, 543, 544, 549, 430/959

[56] References Cited

U.S. PATENT DOCUMENTS

| | | | |
|---|---|---|---|
| 3,253,924 | 5/1966 | Loria et al. | 430/553 |
| 4,248,962 | 2/1981 | Lau | 430/544 |
| 4,390,618 | 6/1983 | Kobayashi et al. | 430/543 |
| 4,463,081 | 7/1984 | Michno | 430/543 |
| 4,471,045 | 9/1984 | Bodem et al. | 430/543 |

FOREIGN PATENT DOCUMENTS 85-191241  9/1985  Japan .

*Primary Examiner*—Richard L. Schilling
*Attorney, Agent, or Firm*—Thomas F. Kirchoff

[57] ABSTRACT

A photographic recording material capable of accelerated development is described. The recording material comprises an image-forming coupler compound, a development inhibitor releasing compound and a compound capable of imagewise release of an electron transfer agent.

8 Claims, No Drawings

PHOTOGRAPHIC RECORDING MATERIAL FOR ACCELERATED DEVELOPMENT

The present invention relates to a photosensitive recording material comprising a compound capable of imagewise release of a development accelerator moiety and a compound capable of imagewise release of a development inhibitor moiety as functions of silver halide exposure and development. More particularly, this invention relates to a photosensitive recording material which provides imagewise release of an electron transfer agent (ETA) moiety capable of selective development acceleration for improved photographic imaging.

The use of development inhibitor releasing compounds in photographic recording materials is well known in the art. This practice generally involves use of a coupler compound which has a development inhibitor moiety bonded to the coupling position of the coupler. The compound is commonly referred to as a DIR coupler, since the development inhibitor moiety is released from the coupler compound as a consequence of a coupling reaction between the coupler and oxidized developing agent.

DIR compounds provide advantages in sharpness and in interimage effects. However, they can cause lower gamma and increased granularity values in subsequently obtained photographic images. Accordingly, the advantages obtained by using DIR compounds can be offset by loss of other desirable photographic properties.

Certain silver halide emulsions are relatively more difficult to develop depending upon their particular physical or chemical properties. For example, larger grain silver halide emulsions, or silver halide grains having relatively higher iodide content, generally develop at slower rates than emulsions having smaller grains or lower iodide content. Methods to accelerate development of exposed silver halide grains have been proposed. For example, U.S. Pat. No. 3,253,924 describes release of a development accelerator moiety from a coupler compound to assist in the normal development process. However, compounds employed in development acceleration frequently cause both increased graininess and fog so that potential advantages can be more than offset by reduced image quality.

More recently, U.S. Pat. No. 4,390,618 describes a method of imagewise development using coupler compounds capable of releasing fogging agents wherein the fogging function is derived from released thiourea, rhodanine, thioamide or, particularly, hydrazide moieties. The desired fogging agent moiety can be released from coupler compounds as the result of a coupling reaction with an oxidation product of a color developing agent.

The desire to control timing of the release of a development accelerator moiety has been recognized and can be accomplished in various ways. For example, U.S. Pat. No. 4,248,962 describes release of photographically useful groups (PUGs) from coupler compounds by means of an intramolecular nucleophilic displacement reaction. Timing groups containing nucleophilic and electrophilic centers are employed which react to effect displacement of auxiliary developing agents and other PUGS from these coupler compounds.

Japanese patent publication No. 85-191,241, published Sept. 28, 1985, describes use of a compound which is capable of reacting with the oxidation product of a developing agent to release a fogging agent moiety, a development accelerator moiety or a precursor of such moiety to obtain improved sensitivity, granularity and sharpness values in subsequently obtained photographic images. As is shown below by comparative data, the combination described in this Japanese Patent Publication fails to yield the desired low fog and granularity values that can be obtained with the present invention.

The methods heretofore employed for accelerating development in photographic recording materials which also comprise DIR compounds have not provided fully satisfactory results. For example, use of hydrazide moieties as auxiliary developing agents has been found to be effective for enhancing dye density at Dmin exposure but to be basically ineffective at Dmax exposure levels. Hydrazide compounds are, in effect, fogging agents and their use is often accompanied by unacceptable levels of fog and background stain in the resulting photographic images.

Accordingly, there exists a need to provide a photographic recording material capable of enhancing silver halide development so as to attain an increase in developed image silver and dye without a concomitant increase in granularity and in fog at minimum image density levels.

The present invention is based upon the discovery that acceleration of silver halide development, without concomitant granularity and fog increase, can be obtained in a photographic recording material comprising a support and a photosensitive silver halide emulsion layer which has, in reactive association therewith, (a) an image dye-forming coupler compound, (b) a compound capable of imagewise release of an electron transfer agent, and (c) a development inhibitor releasing compound, wherein the released electron transfer agent is a 1-aryl-3-pyrazolidinone compound.

A preferred photographic element according to this invention comprises a compound capable of imagewise release of an electron transfer agent which has the structural formula:

$$CAR-(L)_n-ETA$$

wherein:

CAR is a carrier moiety which is capable of releasing —$(L)_n$—ETA on reaction with oxidized developing agent, an especially preferred embodiment of CAR being a coupler moiety COUP which can release —$(L)_n$—ETA during reaction with oxidized primary amine color developing agent;

n is 0, 1, or 2;

L represents a divalent linking group which may be of the same or different type when more than one L moiety is present; and ETA is a 1-aryl-3-pyrazolidinone derivative, attached to L, which upon release from —$(L)_n$—is unblocked and becomes an active electron transfer agent capable of accelerating development under processing conditions used to obtain the desired dye image.

Hereinafter, ETA refers to electron transfer agent and ETARC refers to electron transfer agent releasing compound.

On reaction with oxidized developing agent during processing, the CAR moiety releases the —$(L)_n$—ETA fragment which is capable of releasing an electron transfer agent. The electron transfer agent participates in the color development process to increase the rate of silver halide reduction and color developer oxidation resulting in enhanced detection of exposed silver halide grains and the consequent improved image dye density. Contrary to previously known materials in which a non-cyclic hydrazide fogging agent is released during processing, the ETA moieties released in accordance with this invention provide desirable decreases in image granularity without concomitant fog increases. Depending upon the nature of the —(L)$_n$—moiety in the above-noted structural formula, release of —ETA can be delayed so that the effect of accelerated silver halide development can be more readily controlled.

The electron transfer agent pyrazolidinone moieties which have been found to be useful in providing development acceleration function are derived from compounds generally of the type described in U.S. Pat. Nos. 4,209,580; 4,463,081; 4,471,045; and 4,481,287 and in published Japanese patent application Ser. No. 62-123,172. Such compounds comprise a 3-pyrazolidinone structure having an unsubstituted or a substituted aryl group in the 1-position. Preferably these compounds have one or more alkyl groups in the 4- or 5-positions of the pyrazolidinone ring.

Preferred electron transfer agents suitable for use in this invention are represented by structural formulas I and II:

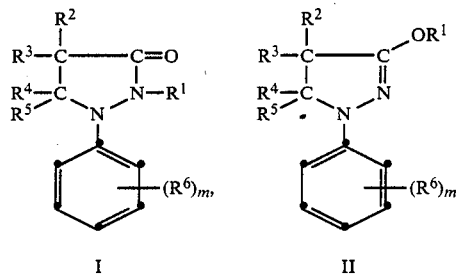

wherein:

$R^1$ is hydrogen;

$R^2$ and $R^3$ each independently represents hydrogen, substituted or unsubstituted alkyl having from 1 to about 8 carbon atoms, such as hydroxyalkyl, carbamoyl, or substituted or unsubstituted aryl having from 6 to about 10 carbon atoms;

$R^4$ and $R^5$ each independently represents hydrogen, substituted or unsubstituted alkyl having from 1 to about 8 carbon atoms or substituted or unsubstituted aryl having from 6 to about 10 carbon atoms;

$R^6$, which may be present in the ortho, meta or para positions of the benzene ring, represents halogen, substituted or unsubstituted alkyl having from 1 to about 8 carbon atoms, or substituted or unsubstituted alkoxy having from 1 to about 8 carbon atoms, or sulfonamido, and when m is greater than 1, the $R^6$ substituents can be the same or different or can be taken together to form a carbocyclic or a heterocyclic ring, including a benzene or an alkylenedioxy ring; and m is 0 to 1 to 3.

When $R^2$ and $R^3$ groups are alkyl it is preferred that they comprise from 1 to 3 carbon atoms. When $R^2$ and $R^3$ represent aryl, they are preferably phenyl.

$R^4$ and $R^5$ are preferably hydrogen.

When $R^6$ represents sulfonamido, it may be, for example, methanesulfonamido, ethanesulfonamido or toluenesulfonamido.

The amount of compound capable of imagewise release of electron transfer agent which can be employed with this invention can be any concentration which is effective for the intended purpose. Good results have been obtained when the compound is employed at a concentration of from about 0.2 to about 1.8 mmols/m$^2$ of photographic recording material. A preferred concentrations is from about 0.5 to about 1.5 mmols/m$^2$.

Especially preferred releasable electron transfer agents, suitable for use in this invention and falling within the above tautomeric structural formulas I and II (where $R^1$ is hydrogen), are presented in Table I:

TABLE I

| ETA No. | $R^2$ | $R^3$ | $R^6$ |
|---|---|---|---|
| 1 | —H | —H | —H |
| 2 | —CH$_3$ | —H | —H |
| 3 | —CH(CH$_3$)$_2$ | —H | —H |
| 4 | —CH$_3$ | —CH$_2$OH | —H |
| 5 | —H | —H | p-CH$_3$ |
| 6 | —H | —H | p-OCH$_3$ |
| 7 | —CH$_3$ | —CH$_2$OH | p-CH$_3$ |
| 8 | —CH$_3$ | —CH$_2$OH | p-OCH$_3$ |

The ETA is attached to the coupler at a position that will cause the ETA to be inactive until released. In structure I or II the point of attachment of the ETA to the CAR, or to the CAR—(L)$_n$—linking moiety, is that point where $R^1$ is attached after release. Such attachment inactivates the ETA moiety so that it is unlikely to cause undesirable reactions during storage of the photographic material. However, the oxidized developer formed in an imagewise manner as a consequence of silver halide development reacts with the CAR moiety to cleave the bond between CAR and L. Thereafter, subsequent reaction, not involving an oxidized developing agent, breaks the bond linking L and the blocked ETA to release the active ETA moiety.

The —(L)—moiety comprises a divalent group by which it is attached to the ETA. Typically, such a group can be

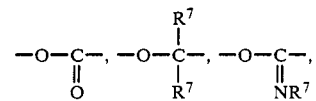

or

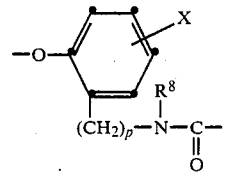

wherein each $R^7$ can independently be hydrogen, alkyl of 1 to about 12 carbon atoms, or aryl of 6 to about 12 carbon atoms;

$R^8$ is alkyl of from 1 to about 20 carbon atoms, preferably lower alkyl of from 1 to about 4 carbon atoms, or aryl of from 6 to about 20 carbon atoms, preferably aryl of from 6 to about 10 carbon atoms; X is —NO$_2$, —CN, sulfone, halogen or alkoxycarbonyl, and p is 0 or 1.

The linking group —(L)$_n$—, where it is present in the compounds described herein, is employed to provide for controlled release of the ETA pyrazolidinone moiety from the coupler moiety so that the effect of accelerated silver halide development can be quickly attained.

Various types of known linking groups can be used. These include quinonemethide linking groups such as are disclosed in U.S. Pat. No. 4,409,323; pyrazolonemethide linking groups such as are disclosed in U.S. Pat. No. 4,421,845; and intramolecular nucleophilic displacement type linking groups such as are disclosed in U.S. Pat. No. 4,248,962 and in European patent application Ser. Nos. 193,389 and 255,085, the disclosures of which are incorporated herein by reference.

Typical useful linking groups include:

L-1
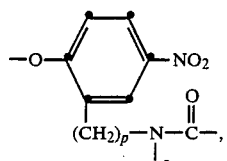

L-2
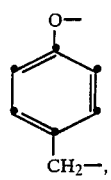

L-3
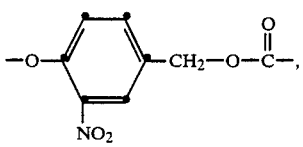

L-4
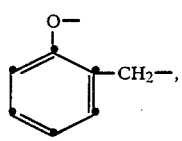

L-5
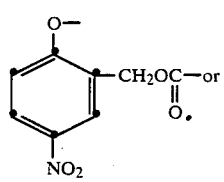

L-6
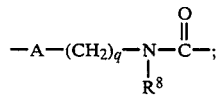

wherein:
A is

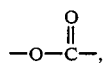

—O—, or —S—;
q is from 1 to 4; and
$R^8$ and p are defined above.

CAR carrier moieties capable, when triggered by reaction with oxidized developing agent, of releasing a photographically useful group (PUG) are particularly well-known in development inhibitor release (DIR) technology where the PUG is a development inhibitor. Typical references to hydroquinone type carriers are U.S. Pat. Nos. 3,379,529, 3,297,445, and 3,975,395. U.S. Pat. No. 4,108,663 discloses similar release from aminophenol and aminonaphthol carriers, while U.S. Pat. No. 4,684,604 features PUG-releasing hydrazide carriers. All of these may be classified as redox-activated carriers for PUG release.

A far greater body of knowledge has been built up over the years on carriers in which a coupler moiety COUP releases a PUG upon reacting with an oxidized primary amine color developing agent. These can be classified as coupling-activated carriers. Representative are U.S. Pat. Nos. 3,148,062, 3,227,554, 3,617,291, 3,265,506, 3,632,345, and 3,660,095.

The COUP, from which the electron transfer agent pyrazolidinone moiety is released, includes coupler moieties employed in conventional color-forming photographic processes which yield colored products based on reactions of couplers with oxidized color developing agents. The couplers can be moieties which yield colorless products on reaction with oxidized color developing agents. The couplers can also form dyes which are unstable and which decompose into colorless products. Further, the couplers can provide dyes which wash out of the photographic recording materials during processing. Such coupler moieties are well known to those skilled in the art.

The COUP moiety can be unballasted or ballasted with an oil-soluble or fat-tail group. It can be monomeric, or it can form part of a dimeric, oligomeric or polymeric coupler, in which case more than one ETA moiety or —(L)$_n$—ETA moiety can be contained in the ETA releasing compound.

Many COUP moieties are known. The dyes formed therefrom generally have their main absorption in the red, green, or blue regions of the visible spectrum. For example, couplers which form cyan dyes upon reaction with oxidized color developing agents are described in such representative patents and publications as: U.S. Pat. Nos. 2,772,162; 2,895,826; 3,002,836; 3,034,892; 2,474,293; 2,423,730; 2,367,531; 3,041,236; 4,333,999; and "Farbkuppler: Eine Literaturübersicht," published in Agfa Mitteilungen, Band III, pp. 156–175 (1961). In the coupler moiety structures shown below, the unsatisfied bond indicates the coupling position to which —(L-)$_n$—ETA may be attached.

Preferably such couplers are phenols and naphthols which form cyan dyes on reaction with oxidized color developing agent at the coupling position, i.e. the carbon atom in the 4-position of the phenol or naphthol. Structures of such preferred cyan coupler moieties are:

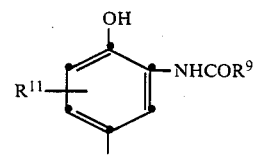

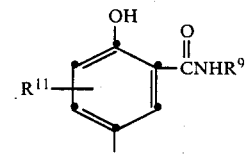

-continued

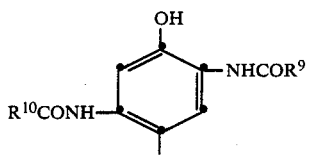

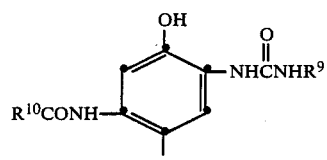

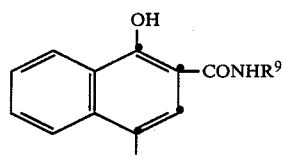

where $R^9$ and $R^{10}$ can represent a ballast group or a substituted or unsubstituted alkyl or aryl group, and $R^{11}$ represents one or more halogen (e.g. chloro, fluoro), alkyl having from 1 to 4 carbon atoms or alkoxy having from 1 to 4 carbon atoms.

Couplers which form magenta dyes upon reaction with oxidized color developing agent are described in such representative patents and publications as: U.S. Pat. Nos. 2,600,788; 2,369,489; 2,343,703; 2,311,082; 3,824,250; 3,615,502; 4,076,533; 3,152,896; 3,519,429; 3,062,653; 2,908,573; 4,540,654; and "Farbkuppler: Eine Literaturübersicht," published in Agfa Mitteilungen, Band III, pp. 126–156 (1961).

Preferably such couplers are pyrazolones and pyrazolotriazoles which form magenta dyes upon reaction with oxidized color developing agents at the coupling position, i.e. the carbon atom in the 4-position for pyrazolones and the 7-position for pyrazolotriazoles. Structures of such preferred magenta coupler moieties are:

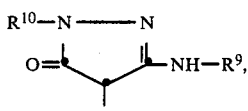

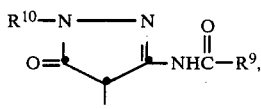

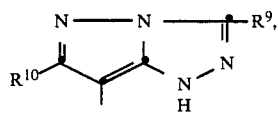

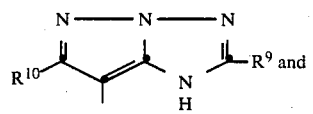

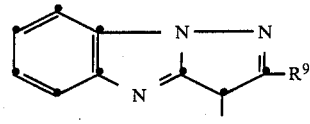

wherein $R^9$ and $R^{10}$ are as defined above; $R^{10}$ for pyrazolone structures is typically phenyl or substituted phenyl, such as for example 2,4,6-trihalophenyl, and for the pyrazolotriazole structures $R^{10}$ is typically alkyl or aryl.

Couplers which form yellow dyes upon reaction with oxidized color developing agent are described in such representative patents and publications as: U.S. Pat. Nos. 2,875,057; 2,407,210; 3,265,506; 2,298,443; 3,048,194; 3,447,928; and "Farbkuppler: Eine Literaturü bersicht," published in Agfa Mitteilungen, Band III, pp. 112–126 (1961).

Preferably such yellow dye-forming couplers are acylacetamides, such as benzoylacetanilides and pivalylacetanilides. These couplers react with oxidized developer at the coupling position, i.e. the active methylene carbon atom.

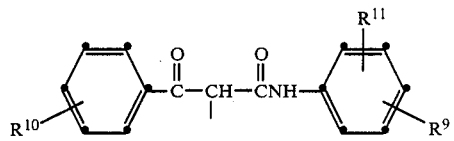

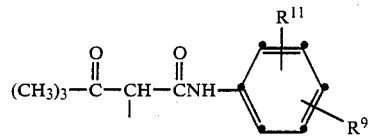

where $R^9$ and $R^{10}$ are as defined above and can also be hydrogen, alkoxy, alkoxycarbonyl, alkanesulfonyl, arenesulfonyl, aryloxycarbonyl, carbonamido, carbamoyl, sulfonamido, or sulfamoyl, $R^{11}$ is hydrogen or one or more halogen, lower alkyl (e.g. methyl, ethyl), lower alkoxy (e.g., methoxy, ethoxy), or a ballast (e.g. alkoxy of 16 to 20 carbon atoms) group.

Couplers which form colorless products upon reaction with oxidized color developing agent are described in such representative patents as: U.K. Pat. No. 861,138 and U.S. Pat. Nos. 3,632,345, 3,928,041, 3,958,993 and 3,961,959. Preferably, such couplers are cyclic carbonyl containing compounds which form colorless products on reaction with oxidized color developing agent and have the L group attached to the carbon atom in the α-position with respect to the carbonyl group.

Structures of such preferred coupler moieties are:

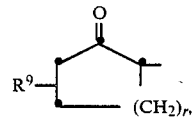

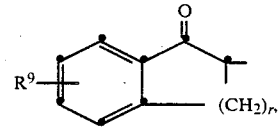

-continued

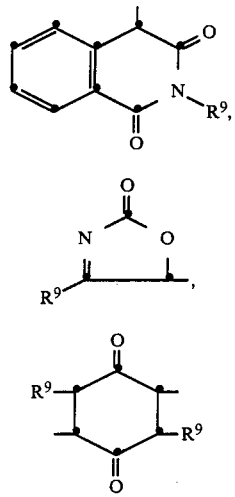

where $R^9$ is as defined above, and r is 1 or 2.

It will be appreciated that, depending upon the particular coupler moiety, the particular color developing agent and the type of processing, the reaction product of the coupler moiety and oxidized color developing agent can be: (1) colored and non-diffusible, in which case it will remain the location where it is formed; (2) colored and diffusible, in which case it may be removed during processing from the location where it is formed or allowed to migrate to a different location; or (3) colorless and diffusible or non-diffusible, in which case it will not contribute to image density. Where it is desirable for such a reaction product to be removable during processing, the groups $R^9$ and $R^{10}$ in the above structures can additionally be hydrogen when attached to an NH group or to a ring carbon atom.

Expecially preferred structures for CAR—$(L)_n$—ETA compounds include the following:

E-1 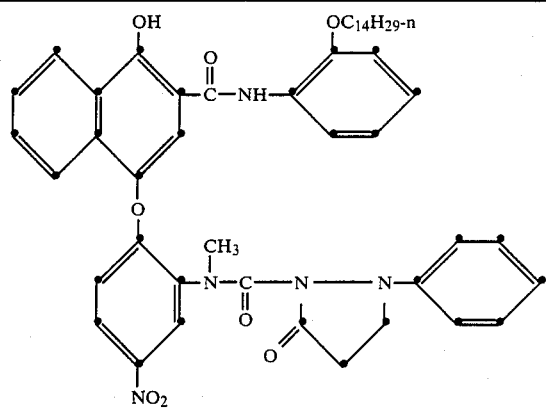

E-2 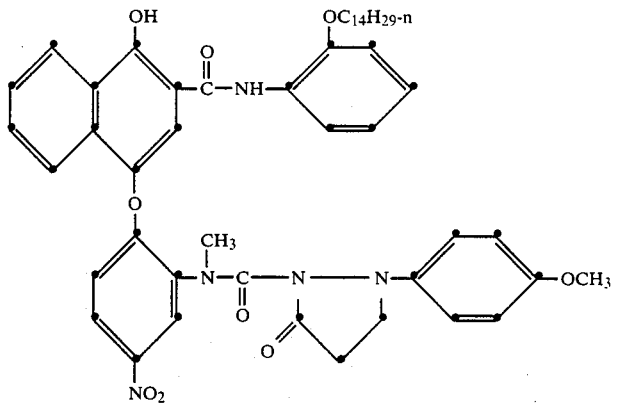

-continued
E-3
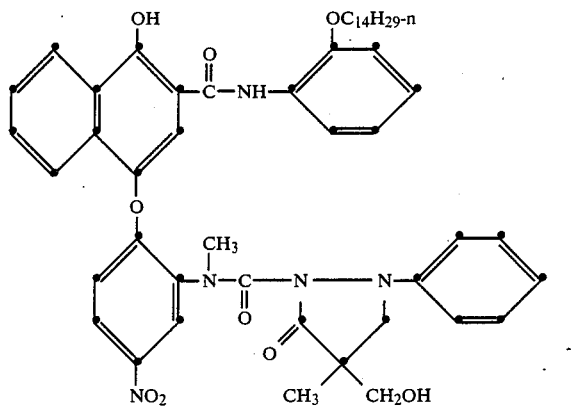
E-4
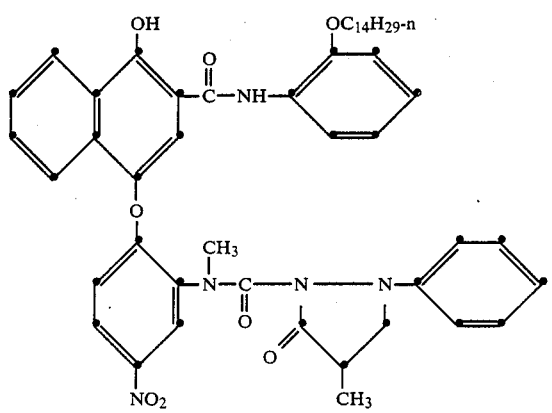
E-5
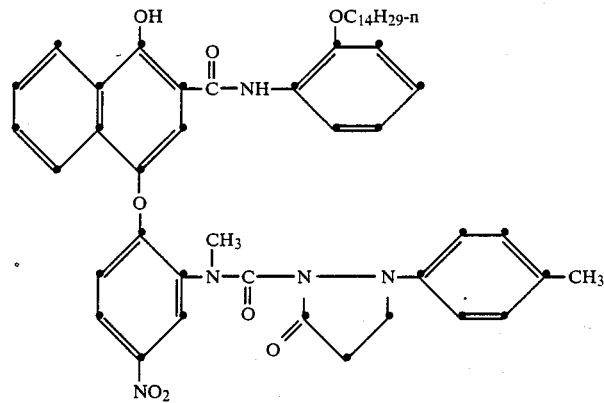
E-6
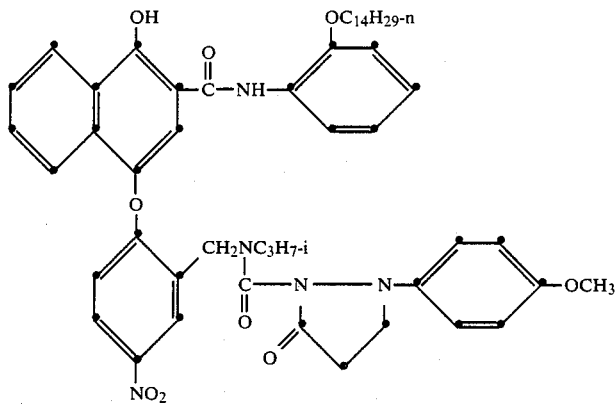

-continued
E-7
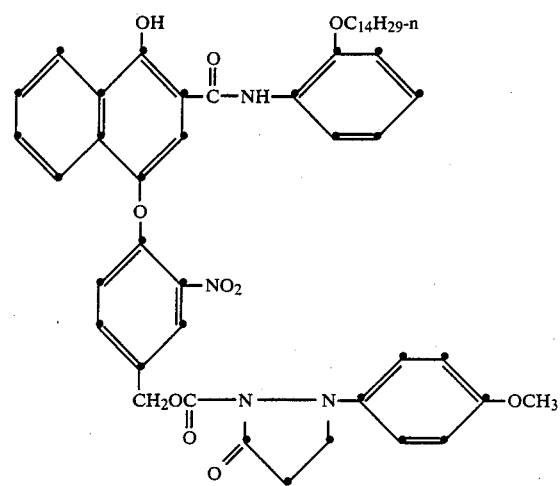
E-8
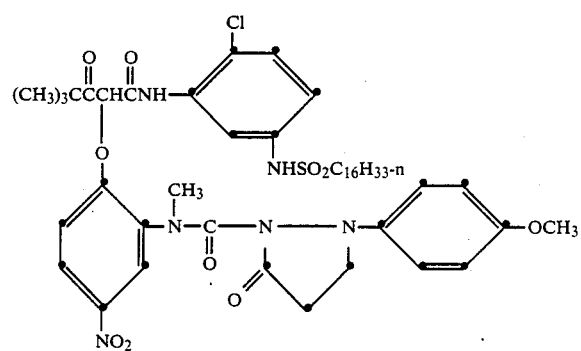
E-9
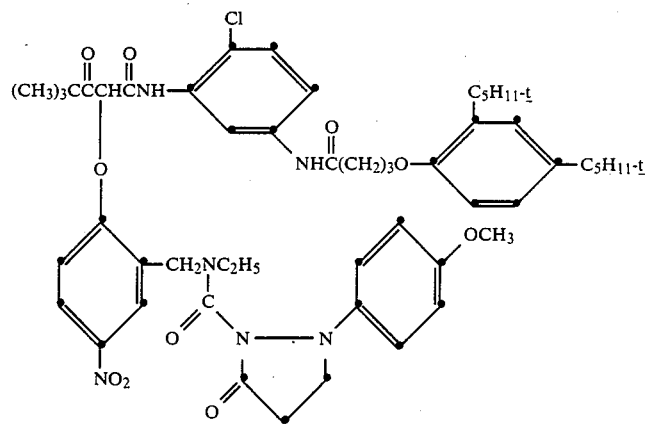

-continued
E-10
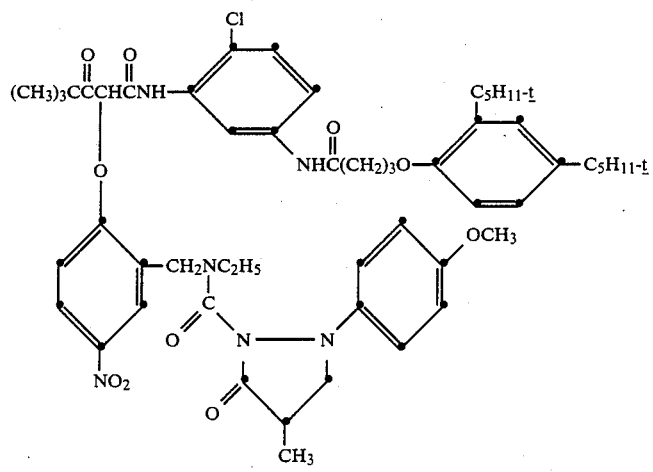
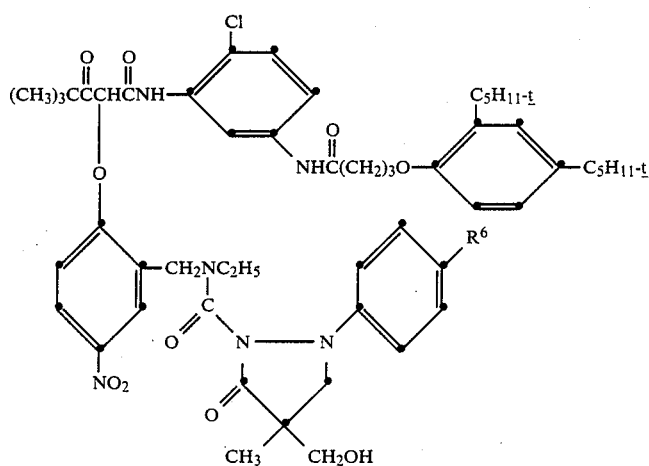
|  | R6 |
|---|---|
| E-11 | —H |
| E-12 | —CH3 |
| E-13 | —OCH3 |
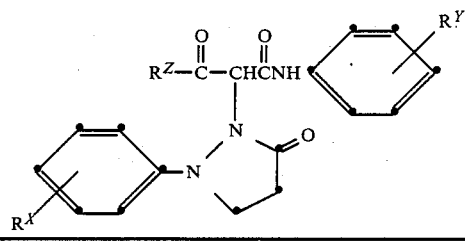
| | RX | RY | RZ |
|---|---|---|---|
| E-14 | —H | m-NHSO2C16H33-n | t-C4H9 |
| E-15 | p-CH3 | m-SO2NHC16H33-n | 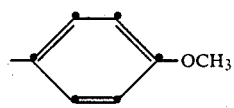 |
| E-16 | p-OCH3 | H |  |

-continued
E-17
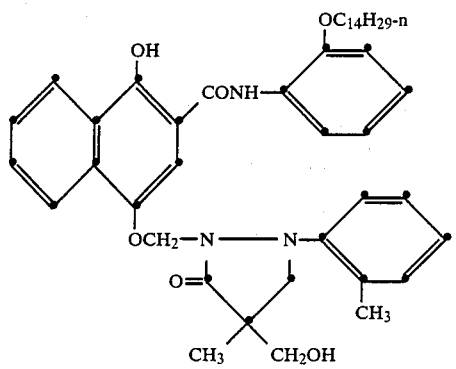
E-18
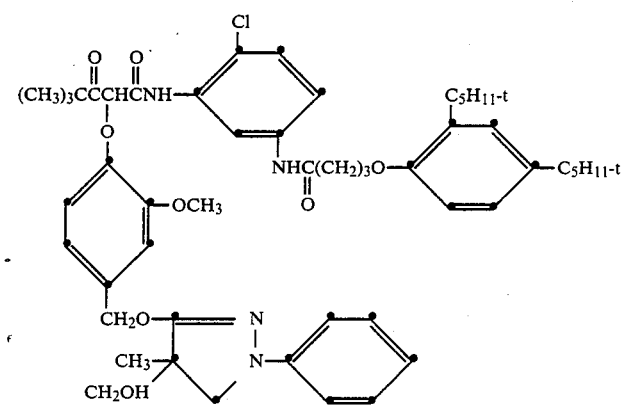
E-19
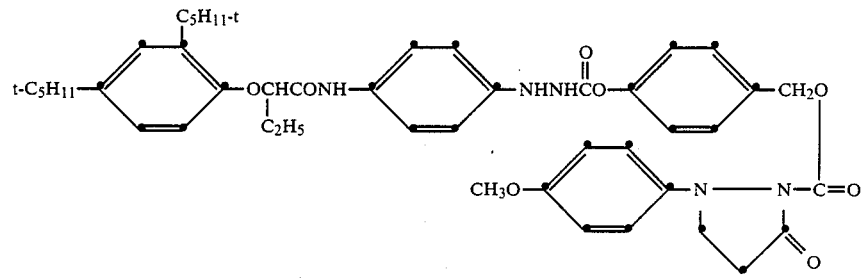
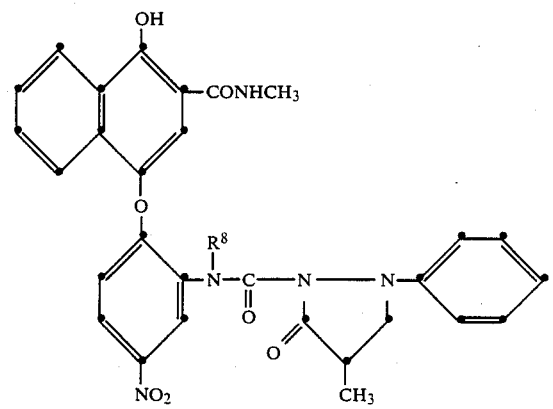
| | $R^8$ |
|---|---|
| E-20 | —$CH_3$ |
| E-21 | —$C_{12}H_{25}$ |

-continued

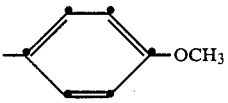

|       | $R^X$   | $R^Y$              | $R^Z$         |
|-------|---------|--------------------|---------------|
| E-22  | —H      | m-NHSO$_2$C$_{16}$H$_{33}$-n | t-C$_4$H$_9$ |
| E-23  | p-CH$_3$ | m-SO$_2$NHC$_{16}$H$_{33}$-n |  —OCH$_3$ |
| E-24  | p-OCH$_3$ | H | 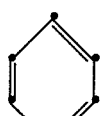 —OCH$_3$ |

Electron transfer agent releasing coupler compounds of this invention can be prepared by several synthetic routes. For example, the ETA can be converted, by treatment with phosgene, to the corresponding carbamoyl chloride which is then caused to react with an amino group or linking moiety attached to a coupler. Where a hydroxy group is present on the ETA, it is typically protected by a blocking group (e.g. a silyl group) during reaction of the ETA with phosgene. The blocking group can later be removed by reaction with an acidic hydrolyzing agent, such as for example trifluoroacetic acid. The following synthesis of ETA compound E-3, as shown above, is prepared by this procedure.

Synthesis No. 1

Preparation of electron transfer agent releasing Compound E-3:

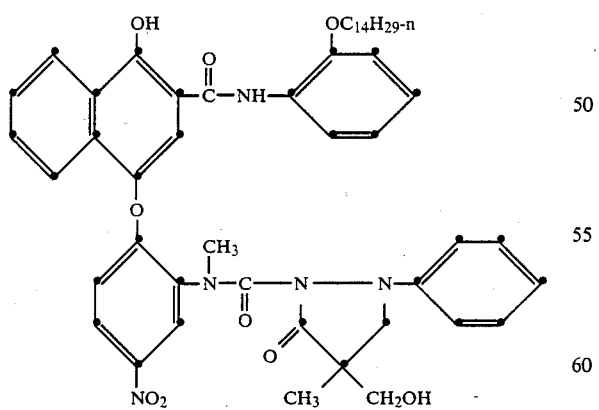

A schematic representation of the reactions involved in this synthesis is as follows:

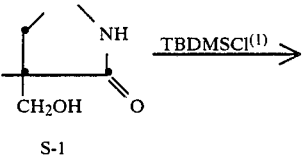

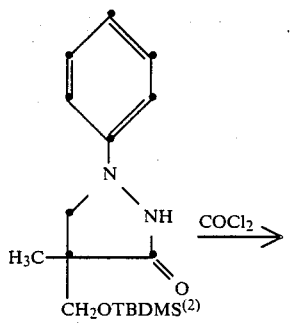

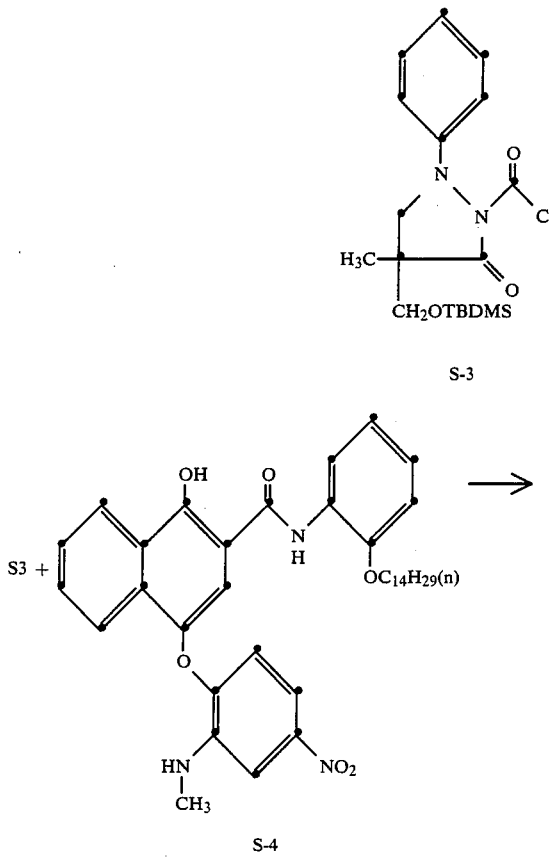

S-3

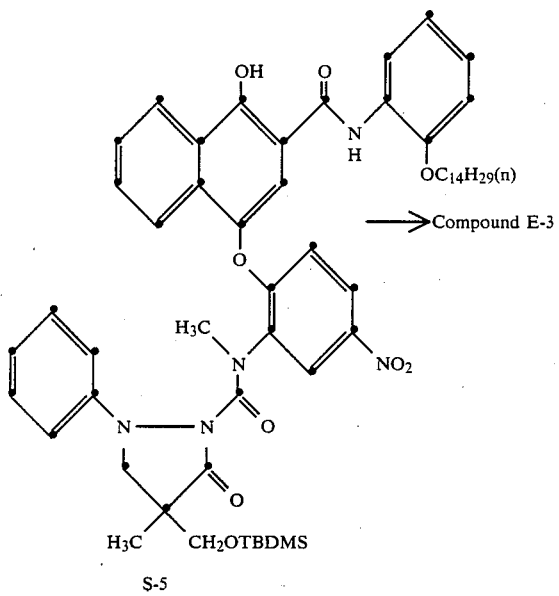

S-4

(1) TBDMSCl refers to t-butyldimethylsilylchloride.
(2) TBDMS refers to t-butyldimethylsilyl.

S-5

Synthesis of Intermediate S-2

Under nitrogen, solid t-butyldimethylsilylchloride (TBDMSCl), 18.1 g, 0.12 mole was added in one portion to a stirred solution of S-1 (20.5 g, 0.10 mol) and imidazole (17.0 g, 0.25 mole) in 100 ml of anhydrous N,N-dimethylformamide. After 5.0 hours, the mixture was poured into cold dilute HCl(aq) and extracted repeatedly with ethyl acetate. The combined extracts were washed with saturated sodium chloride(aq), dried over MgSO$_4$ (anhydrous) and concentrated in vacuum. The residue was digested in mixed hexanes and a small amount of residual starting material was removed by filtration. The filtrate was concentrated at reduced pressure, slurried in mixed hexanes, and cooled in an ice-/acetone bath. The precipitate was collected by filtration, and air dried to yield 13.2 g (41.0%) of a white solid. The NMR spectrum was consistent with the proposed structure for S-2.

Synthesis of Intermediate S-3

Under nitrogen, a solution of S-2 (13.2 g, 0.04 mole) and diisopropylethylamine (7.2 ml, 0.04 mole) in 60 ml of CH$_2$Cl$_2$ was added dropwise to a stirred, $-78°$ C. solution of phosgene (60 ml of a 15% solution in toluene) in 60 ml of CH$_2$Cl$_2$. The mixture was allowed to stir for 60 minutes at $-78°$ C., treated with 2 ml of concentrated HCl, diluted with CH$_2$Cl$_2$, washed with dilute ($\approx$10.0%) HCl, then with saturated NaCl (aq), and dried over MgSO$_4$ (anhydrous). The solvent was removed at reduced pressure and the residue digested in hexane. The solution was cooled to $-78°$ C. and the solid formed by precipitation was collected by filtration to yield S-3 (11.0 g, 72%) as a white solid.

Synthesis of Intermediate S-5

Under nitrogen, a stirred, room temperature solution of S-4 (13.5 g, 0.021 mol) and of S-3 (11.0 g, 0.029 mol) in 100 ml of anhydrous THF was treated with N,N-dimethylaniline (13.3 ml, 0.11 mol) and allowed to stir overnight. The mixture was diluted with a three-fold volume of dilute HCl and the mixture extracted with ethyl acetate. The separated organic phase was washed with saturated NaCl(aq), dried over MgSO$_4$ (anhydrous) and freed of solvent at reduced pressure. The residue was chromatographed on silica gel and freed of solvent to yield S-5 as an oil which was used directly in the preparation of Compound E-3

Synthesis of Compound E-3

Under nitrogen, a solution of S-5 in 100 ml of THF was treated, with stirring and at room temperature, with 5 ml of trifluoroacetic acid (TFA). The mixture was allowed to stir for 18 hours at room temperature, treated with an additional 5 ml of TFA and allowed to stir for an additional 74 hours. The mixture was poured into water and extracted with ethyl acetate. The combined organic phase was washed with saturated NaCl(aq), dried over MgSO$_4$ (anhydrous) and freed of solvent at reduced pressure. The residue was chromatographed on silica gel to yield Compound E-3 (12.1 g) as a pale yellow solid (mp: 132.5°–135.0° C.), after crystallization. The analytical and spectral data for this product are in accord with the proposed structure.

Synthesis No. 2

Preparation of electron transfer agent releasing Compound E-2:

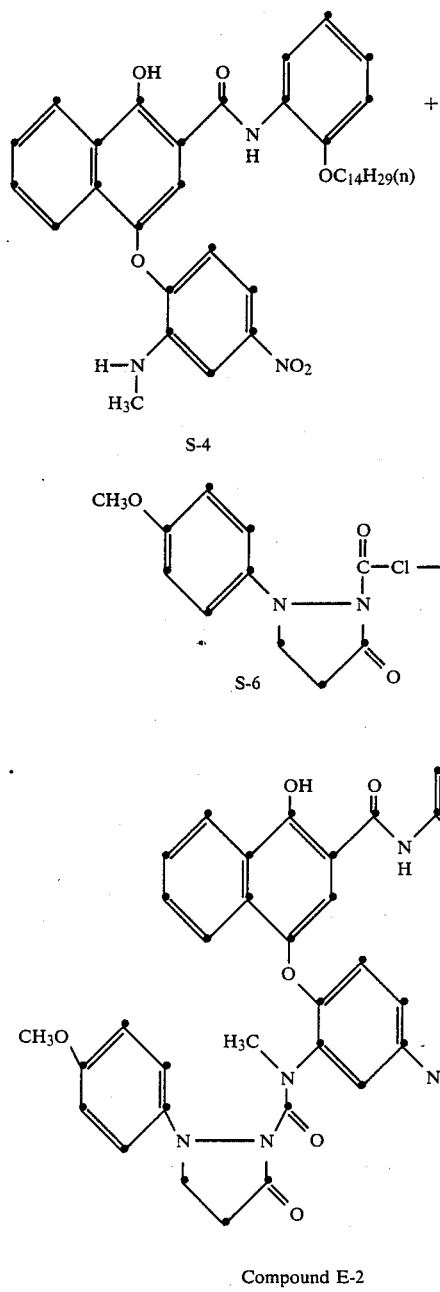

Compound E-2

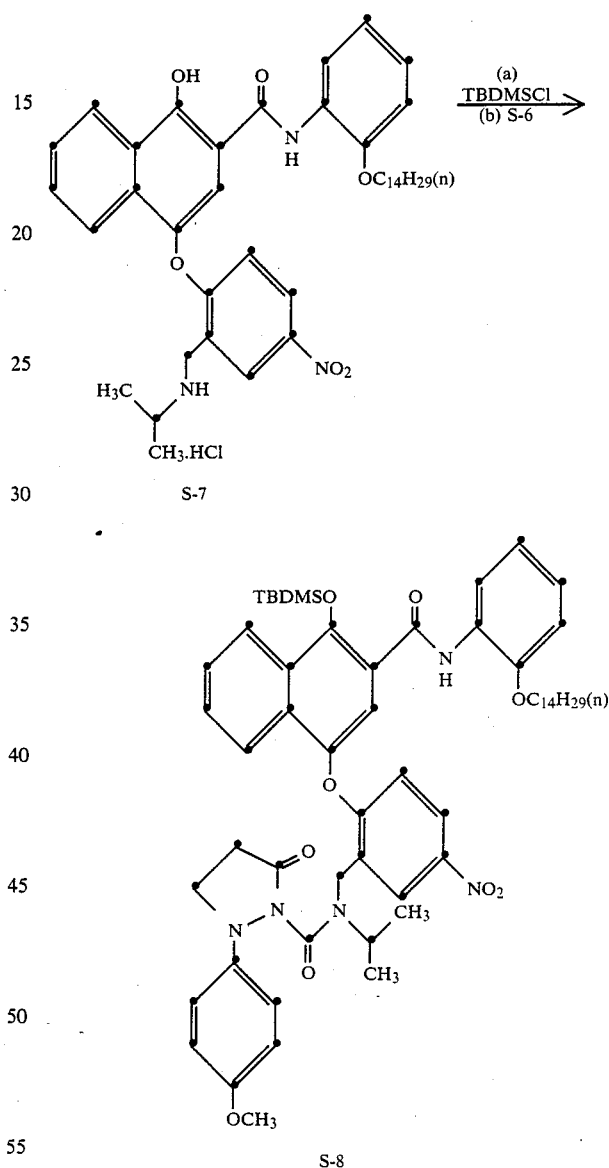

44.2 g (66.0%) of a pale yellow solid. Both spectral (NMR, IR, MS) and analytical data, including elemental analysis and high pressure liquid chromatography, are in agreement with the proposed structure of Compound E-2.

Synthesis No. 3

Preparation of electron transfer agent releasing Compound E-6:

Under nitrogen, solid ETA carbamoyl chloride S-6 (35.8 g, 0.14 mole) was added to a stirred room temperature solution of S-4 (50.0 g, 0.078 mole) and N,N-dimethylaniline (50.0 ml, 0.39 mole) in 800 ml of anhydrous tetrahydrofuran (THF). The mixture was allowed to stir overnight at room temperature, poured into dilute ($\approx$5.0%) HCl (aq) and extracted with ethyl acetate. The combined ethyl acetate extracts were washed with brine, dried over MgSO$_4$ (anhydrous) and freed of solvent at reduced pressure. The residue was chromatographed on silica gel using methylene chloride as the eluting solvent; fractions corresponding to E-2 were united and freed of solvent at reduced pressure. The residual yellow oil was dissolved in anhydrous diethyl ether and stirred at room temperature for 2.0 hours. The solid that precipitated was collected by filtration, washed with cold diethyl ether, and air dried to yield Synthesis of Intermediate S-8

Under nitrogen, a solution of S-7 (7.19 g, 0.01 mol) in a combination of 50 ml THF and 25 ml ethyl acetate was treated with a solution of saturated NaHCO$_3$ (aq) with vigorous stirring. After 5 minutes, the separated organic layer was washed with saturated NaCl (aq), dried over MgSO$_4$ (anhydrous), and freed of solvent at reduced pressure. The residue was digested in 25 ml DMF and under nitrogen with stirring, treated sequentially with tert-butyldimethylsilyl chloride (1.81 g, 0.012 mol), and imidazole (1.70 g, 0.025 mol). The mixture was allowed to stir for 14 hours at room temperature, diluted with 200 ml of water and extracted with ethyl acetate. The combined ethyl acetate extracts were washed with liberal amounts of water, then with saturated NaCl (aq), dried over MgSO₄ (anhydrous), and freed of solvent at reduced pressure to yield 7.25 g of a dark red oil. The latter was dissolved in 50 ml of CH₃CN and 5 ml of CH₂Cl₂. Under nitrogen, with stirring, the solution was sequentially treated with 2,6-lutidine (1.07 g, 0.01 mol) and S-6 (2.29 g, 0.009 mol) and allowed to stir for 1.0 hour at room temperature. The mixture was diluted with ethyl acetate, washed with dilute HCl (aq), dried over MgSO₄ (anhydrous), and freed of solvent at reduced pressure. The residue was chromatographed on silica gel using hexane/ethyl acetate as the eluting solvent to yield S-8 (5.65 g, 63.9%) as a pale yellow foamy solid. Spectral and analytical data are in accord with the proposed structure.

Synthesis of Compound E-6:

Under nitrogen, a solution of S-8 (3.05 g, 0.003 mol) in 80 ml of THF was treated sequentially with 20 ml of H₂O and 1 ml of trifluoroacetic acid and allowed to stir for 8 hours at room temperature. The mixture was diluted with ethyl acetate and the separated organic layer was washed with saturated NaHCO₃ (aq), then with saturated NaCl (aq), and dried over MgSO₄ (anhydrous). The solvent was removed at reduced pressure and the residue was crystallized from ethyl acetate/hexane to yield Compound E-6 (2.64 g, 97.6%) as an off-white solid. Spectral and analytical data are in accord with the proposed structure.

Synthesis No. 4

Preparation of electron transfer agent releasing Compound E-10:

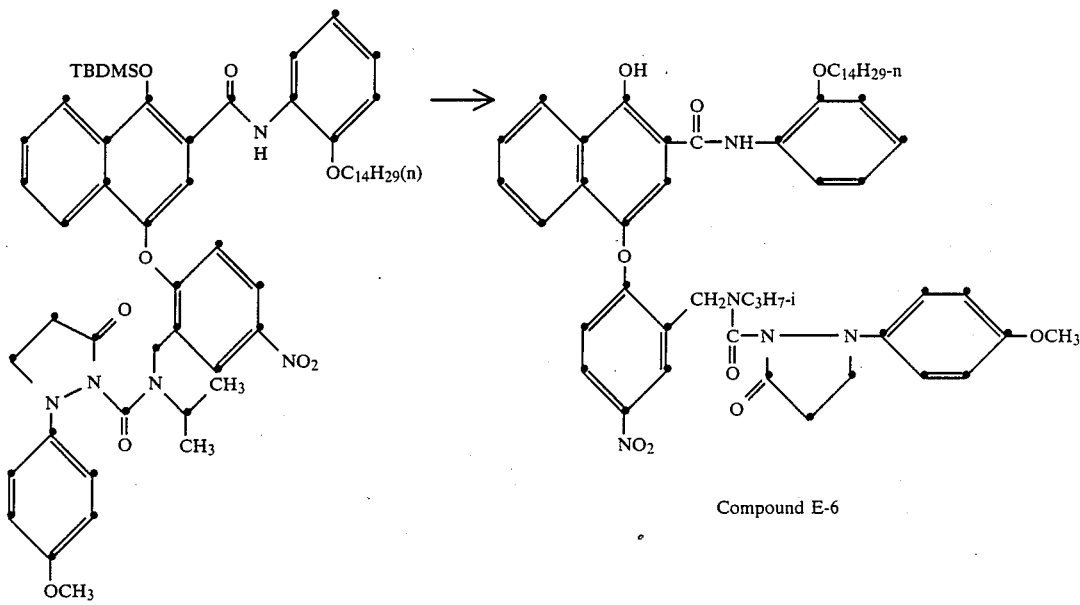

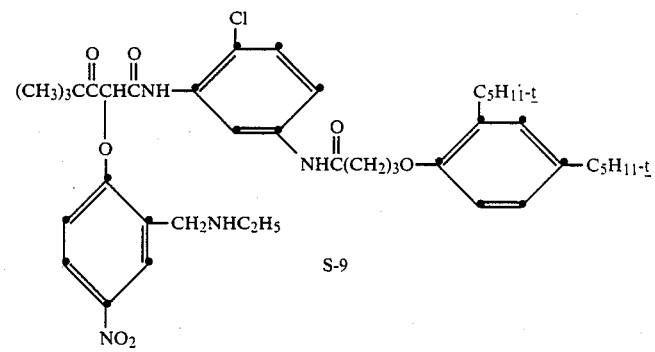

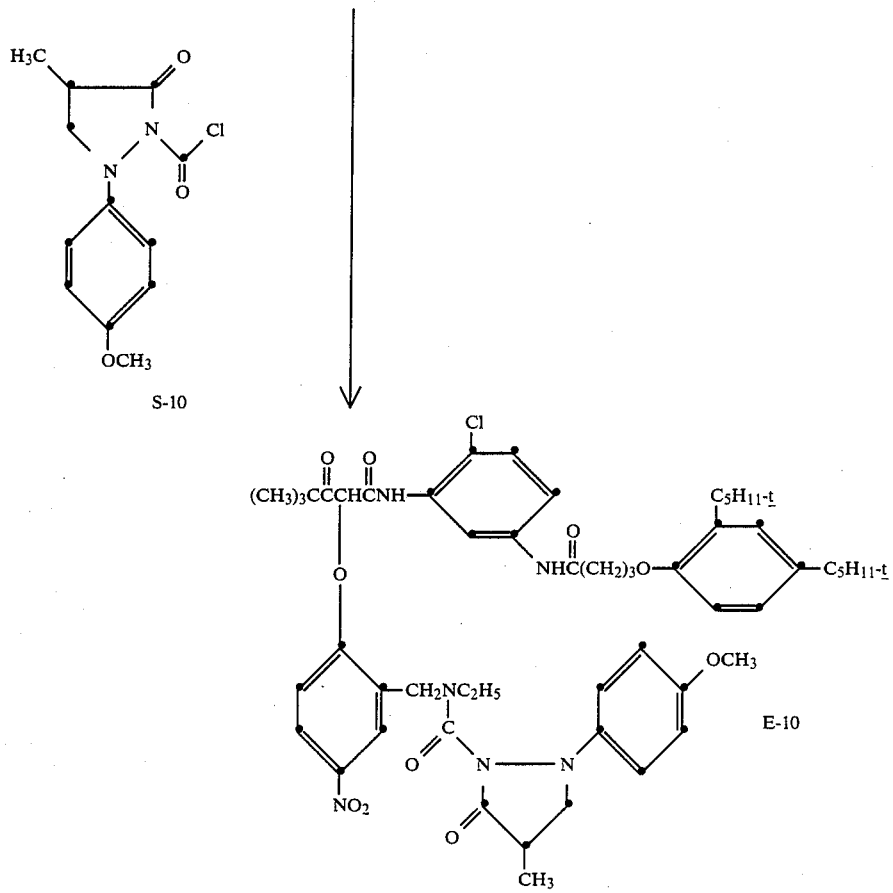

Synthesis of Compound E-10

Under nitrogen, solid S-10 (2.02 g, 0.0075 mol) was added to a stirred slurry of S-9 (6.01 g, 0.015 mol) in 80 ml of CH$_3$CN. The mixture was allowed to stir for 1.0 hour at room temperature, washed with cold dilute HCl (aq), then with saturated NaCl (aq), dried over MgSO$_4$ (anhydrous). The solvent was removed at reduced pressure and the residue was precipitated from a mixture of diethyl ether/ethyl acetate/hexane. The solid obtained was recrystallized from hexane/ethyl acetate to yield Compound E-10 (5.63 g, 75.0%) as an off-white solid. Spectral and analytical data are in accord with the proposed structure.

The development inhibitor releasing (DIR) compound to be used in conjunction with the ETA releasing compound according to this invention, can be selected from those known in the art. These include both the direct release DIR compounds and the timed release DIR compounds of the general structure CAR—(L-)$_n$—In, wherein CAR is a carrier moiety which can be a redox releasing moiety or a COUP as defined above; —(L)$_n$—can be as defined above; and In is a development inhibitor moiety. References describing development inhibitor-releasing (DIR) compounds include U.S. Pat. Nos. 3,148,062; 3,227,554; 3,733,201; 3,617,291; 3,980,479; 3,933,500; 4,248,962; 4,409,323 and 4,684,604, the disclosures of which are hereby incorporated by reference. Specific structures of useful DIR compounds are shown in the photographic examples below.

The ETA releasing compound, the development inhibitor-releasing (DIR) compound, and the dye image-forming coupler compound, all of which are in reactive association with a silver halide layer of a light-sensitive photographic recording material, upon reaction with oxidized color developing agent, can yield dyes of various colors. Alternatively, dyes formed from the ETA releasing compound or DIR compound can be colorless or can be washed out of the photographic recording material during processing. More than one DIR, ETA releasing compound, or image coupler can be employed in a given color-forming unit comprising one or more silver halide layers and typically producing, during processing, a yellow, magenta, or cyan dye image. It is usually preferable, although not required, that the components of a given color-forming unit produce dyes absorbing in the same spectral region.

The photographic recording materials of this invention in which the described compounds are incorporated can comprise a support and one or more silver halide emulsion layers. The compounds are preferably incorporated in a silver halide emulsion layer. However, one or more of these compounds can be incorporated in another layer, such as a layer adjacent to a silver halide layer, where they will come into reactive association with oxidized color developing agent formed during silver halide development. Additionally, a silver halide emulsion layer and an adjacent layer containing one or more of the compounds can contain addenda conventionally contained in such layers.

The practice of this invention is possible in single color or in multicolor image-recording materials. The invention is useful in a variety of layer arrangements well known in the art.

In a preferred embodiment, the recording material of this invention is multicolor and comprises a support having thereon a red-sensitive silver halide emulsion layer having associated therewith a cyan image dye-forming coupler compound, a green-sensitive silver halide emulsion layer having associated therewith a magenta image dye-forming coupler compound, and a blue-sensitive silver halide emulsion layer having associated therewith a yellow image dye-forming coupler compound, at least one of said emulsion layers also having associated therewith a compound capable of imagewise releasing an electron transfer agent and an imagewise development inhibitor releasing compound.

In the following discussion of suitable materials for use in the photographic recording material of this invention, reference is made to Research Disclosure, Dec. 1978, Item 17643, published by Industrial Opportunities Ltd., Homewell Havant, Hampshire, P09 1EF, U.K., the disclosures of which are incorporated herein by reference. This publication will be identified hereafter by the term "Research Disclosure".

The silver halide emulsions employed in this invention can be either negative-working or positive-working. Suitable emulsions and their preparation are described in Research Disclosure Sections I and II, and the publications cited therein, and can include coarse, medium or fine grains or mixtures thereof. The grains may be of different morphologies, e.g., spherical, cubic, cubooctrahedral, tabular, etc., or mixtures thereof. Grain size distribution may be monodisperse or polydisperse or mixtures thereof.

Such silver halides include silver chloride, silver bromide, silver iodide, silver bromoiodide, silver chlorobromide, silver chloroiodide, silver chlorobromoiodide and mixtures thereof. The emulsions can form latent images predominantly on the surface of the silver halide grains or predominantly in the interior of the grains. They can be chemically and spectrally sensitized. The emulsions preferably contain gelatin, although other natural or synthetic hydrophilic colloids, soluble polymers or mixtures thereof can be used.

Suitable vehicles for the emulsion layers and other layers used in the recording materials of this invention are described in Research Disclosure Section IX and the publications cited therein.

In addition to the compounds described herein the recording materials of this invention can include additional couplers as described in Research Disclosure Section VII, paragraphs D, E, F and G and the publications cited therein.

The recording materials of this invention can contain brighteners (Research Disclosure Section V), antifoggants and stabilizers (Research Disclosure Section VI), antistain agents and image dye stabilizers (Research Disclosure Section VII, paragraphs I and J), light absorbing and scattering materials (Research Disclosure Section VIII), hardeners (Research Disclosure Section XI), plasticizers and lubricants (Research Disclosure Section XII), antistatic agents (Research Disclosure Section XIII), matting agents (Research Disclosure Section XVI) and development modifiers (Research Disclosure Section XXI).

The recording materials can be coated on a variety of supports as described in Research Disclosure Section XVII and the references described therein.

The described recording materials can be exposed to actinic radiation, typically in the visible region of the spectrum, to form a latent image as described in Research Disclosure Section XVIII and then processed to form a visible dye image as described in Research Disclosure Section XIX. Processing can be accomplished by conventional techniques which include treating an imagewise-exposed element with an alkaline processing solution containing a color developing agent (and another developing agent, if desired). Particularly useful color developing agents include aminophenols, phenylenediamines, tetrahydroquinolines as described, for example, in Research Disclosure Section XX, the disclosures of which are incorporated herein by reference. Other compounds including hydroquinones and catechols are useful as auxiliary developing agents.

The term "associated therewith" as used herein is intended to mean that the materials can be in either the same or different layers so long as the materials are accessible to one another.

The following examples illustrate the photographic advantages obtainable with compounds of the invention. All percents and ratios are by weight unless otherwise specified.

EXAMPLES 1–15

A dispersion of each electron transfer agent releasing compound (ETARC) was prepared according to the following formula:

ETARC (1%), N,N-diethyl dodecanamide (2%), ethyl acetate (3%), gelatin (6%), and Alkanol XC wetting agent (0.6%).

Then photographic recording materials were prepared by coating the following layers on a cellulose ester film support (each ETARC was coated at 0.215 mmoles/m$^2$; amounts of other components are indicated in mg/m$^2$):

Emulsion Layer 1: gelatin-2691; green-sensitized silver bromoiodide (3 mol % I) emulsion (as Ag)-807; cyan image coupler C-1 -807 (unless otherwise indicated) dispersed in dibutyl phthalate; DIR compound and ETARC as indicated in Tables II or III Interlayer: gelatin-646; didodecylhydroquinone -129

Emulsion Layer 2: gelatin-2691; red-sensitized silver bromoiodide (3 mol % I) emulsion (as Ag)-807; yellow image coupler Y-1-1292 dispersed in dibutyl phthalate Protective Overcoat: gelatin-5382; bisvinylsulfonylmethyl ether at 2% of total gelatin Structures of image couplers C-1 and Y-1 and DIR couplers D-1 through D-4 are as follows:

| Couplers | Structure |
| --- | --- |

C-1:
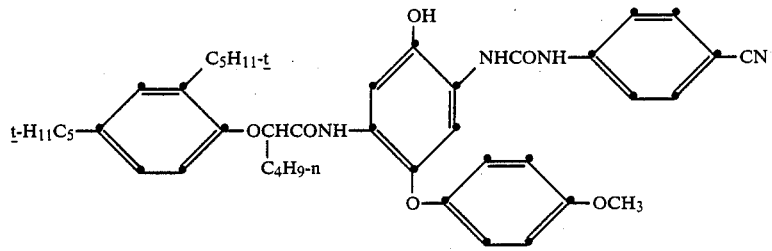
Y-1:
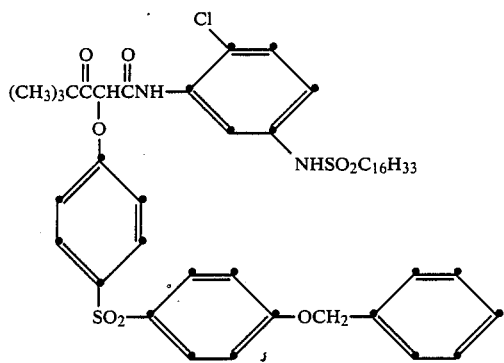
Development Inhibitor-Releasing (DIR) Compounds
D-1:
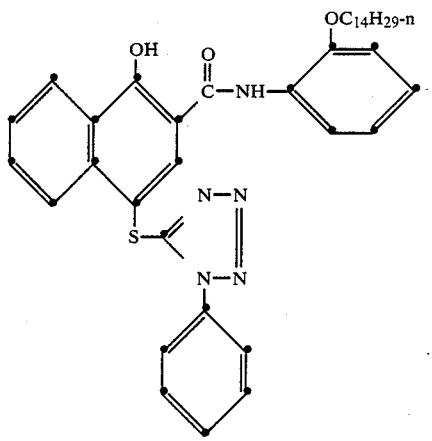
D-2:
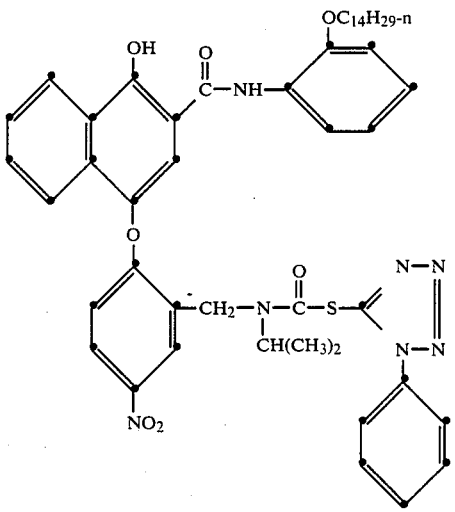

-continued

D-3:
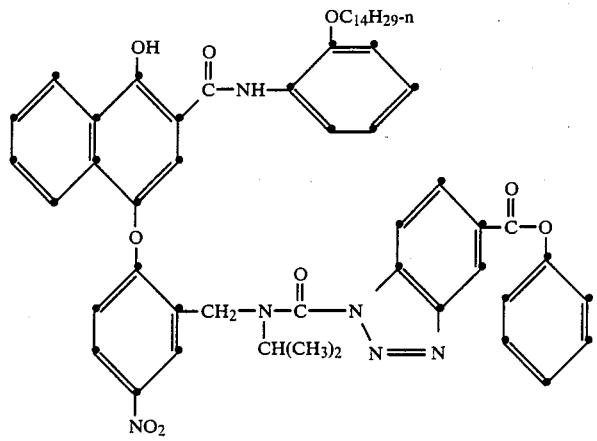

D-4:
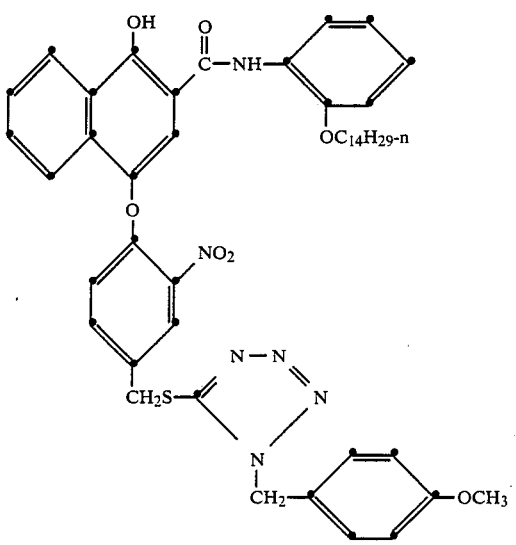

Strips of each element were given a 5500° K. stepwise exposure and developed in the process described in the British Journal of Photography 1982 Annual, page 209, (which includes development using a p-phenylenediamine type compound) the description of which is incorporated herein by reference. Responses of the processed images to red light were measured to obtain contrast, granularity and sharpness data. The contrast of the sensitometric curves obtained is reported as "G" (gamma) in the following tables. In Table II, the measured granularity of a given step was normalized by dividing the incremental gamma at that step and multiplying by 1000 to obtain the result reported as "grain". In Table III, the granularity for each Example was measured at two different exposure steps (a and b) and then normalized by dividing the incremental gamma value at that step and multiplying by 1000 to obtain the "grain" result.

Sharpness or acutance was measured as described by Lamberts and Eisen in the Journal of Applied Photographic Engineering, Vol. 6, pp. 1-8 (1980) and is reported as percent MTF (Modulation Transfer Function), typically measured at 5 cycles/mm. Tables II and III reflect the results.

TABLE II

| Ex. No. | Coupler* (mg/m$^2$) | DIR* (mg/m$^2$) | ETARC* | G | Grain | MTF |
|---|---|---|---|---|---|---|
| 1 Comp. | 915 | 22 | — | 1.15 | 17.15 | 99.0 |
| 2 Inv. | 915 | 22 | E-2 | 1.43 | 13.50 | 100.4 |
| 3 Comp. | 807 | 32 | — | 0.81 | 19.68 | 109.7 |
| 4 Inv. | 807 | 32 | E-1 | 1.11 | 16.69 | 108.1 |
| 5 Inv. | 807 | 32 | E-3 | 1.14 | 16.68 | 110.2 |
| 6 Comp. | 807 | 54 | — | 0.53 | 24.78 | 115.8 |
| 7 Inv. | 807 | 54 | E-1 | 0.81 | 20.55 | 114.3 |
| 8 Inv. | 807 | 54 | E-3 | 0.79 | 19.67 | 105.8 |

*Cyan coupler is C-1 and DIR coupler is D-4, each as described above; each ETA releasing compound was coated at 0.215 mmole/m$^2$.

The data in Table II show that addition of an ETA releasing compound, according to this invention, to an image coupler in combination with a DIR coupler at several different coating levels results in a higher gamma (showing development acceleration) and lower granularity. A comparison of Examples 1 and 5 indicates that sharpness can be improved and granularity decreased at the same gamma by increasing the DIR level and adding an ETA releasing compound of this invention.

TABLE III

| Ex. No. | DIR (mg/m²) | ETARC* | G | Step a Grain | G | Step b Grain | MTF |
|---|---|---|---|---|---|---|---|
| 9 Control | None | — | 1.75 | 10.5 | 1.63 | 11.7 | 91.6 |
| 10 Comp. | D-1 (22) | — | 1.00 | 11.3 | 0.93 | 13.9 | 101.2 |
| 11 Inv. | D-1 (22) | E-2 | 1.13 | 10.3 | 1.05 | 12.1 | 94.3 |
| 12 Comp. | D-2 (38) | — | 0.65 | 14.2 | 0.58 | 18.5 | 107.3 |
| 13 Inv. | D-2 (38) | E-2 | 0.80 | 11.5 | 0.71 | 14.6 | 94.9 |
| 14 Comp. | D-3 (63) | — | 1.23 | 11.9 | 1.08 | 14.6 | 103.8 |
| 15 Inv. | D-3 (63) | E-2 | 1.27 | 10.8 | 1.18 | 12.4 | 100.0 |

*Compound E-2 was coated at 0.215 mmols/m²

It can be seen from the comparison Examples 10, 12 and 14 in Table III that when several different DIR couplers are added to a coating containing an image coupler, a severe granularity price is paid to gain the desired sharpness in the resultant images. However, employing a DIR/ETARC combination according to this invention allows an improvement in sharpness with little or no net granularity increase. For each DIR example, addition of the ETA releasing compound caused development acceleration resulting in a gamma increase and 10–20% reduction in granularity.

EXAMPLES 16–20

Photographic recording materials were prepared and processed in a manner similar to that for Examples 1–15 above, except that the layers were coated in a different layer order and were stepwise exposed to green light using a Wratten 99 filter. The developed images were read with red light to obtain the results reported in Table IV. The following layers were coated on a cellulose ester film support (coated amounts of components are indicated in mg/m²):

Emulsion layer 1: Gelatin-2691; Red-sensitized silver bromoiodide (3 mol % I) emulsion (as Ag)-1615; Yellow image coupler Y-1-1292 dispersed in dibutyl phthalate Interlayer: Gelatin-646; didodecylhydroquinone-129

Emulsion Layer 2: Gelatin-2691; Green-sensitized silver bromoiodide (3 mol % I) emulsion (as Ag)-807; Cyan image coupler C-2-753 dispersed in dibutyl phthalate; hydrazide releasing compound and ETARC as indicated in Table IV Protective Overcoat: Gelatin-5382; Bisvinylsulfonylmethyl ether at 2% of total gelatin Yellow image Coupler Y-1 is described above.

Structures of image coupler C-2 and hydrazide-releasing compound F-1 (of a type described, for example in Japanese patent application Ser. No. 85-191,241) are as follows:

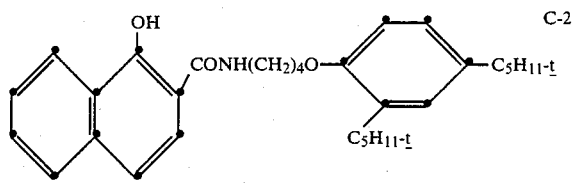

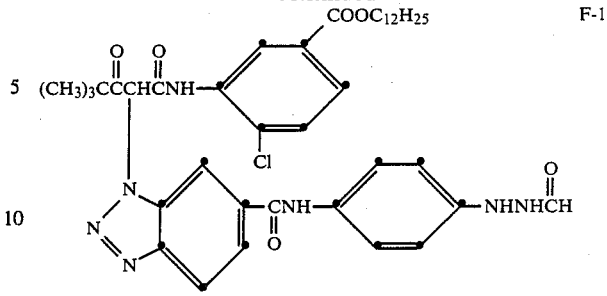

TABLE IV

| Example No. | Addendum | (mg/m²) | Dmin | Dmax | Grain |
|---|---|---|---|---|---|
| 16 Control | None | — | 0.17 | 1.35 | 13.1 |
| 17 Comp. | F-1 | 8.2 | 0.20 | 1.33 | 14.8 |
| 18 Comp. | F-1 | 16.4 | 0.30 | 1.29 | 20.3 |
| 19 Inv. | E-2 | 92.6 | 0.17 | 1.42 | 13.0 |
| 20 Inv. | E-2 | 185.2 | 0.18 | 1.51 | 12.4 |

An examination of the Dmin values in the above table shows that addition of a prior art type hydrazide releasing compound, Comparison F-1, even at low levels, produces undesirable fog. Doubling the level of F-1 increases fog and graininess without increasing the image Dmax. Use of Compound E-2 of the invention, however, gives a desired Dmax increase, while maintaining fog and graininess values at desirably low levels. Adding higher amounts of Compound E-2 has little, if any, effect on fog.

Reference is made to copending application Ser. No. 209,611, filed Jun. 21, 1988, entitled "PHOTOGRAPHIC RECORDING MATERIAL PROVIDING IMPROVED GRANULARITY PROPERTIES", of Platt et al, filed concurrently herewith, the disclosure of which is incorporated herein by reference.

This invention has been described in detail with particular reference to preferred embodiments thereof, but it will be understood that variations and modifications can be effected within the spirit and scope of the invention.

What is claimed:

1. A photographic recording material comprising a support and a photosensitive silver halide emulsion layer which has, in reactive association therewith,
   (a) an image dye-forming coupler compound,
   (b) a compound capable of imagewise release of an electron transfer agent upon reaction with oxidized primary amine color developing agent, and
   (c) a development inhibitor-releasing compound, wherein the compound capable of imagewise release of an electron transfer agent has the formula:

$$\begin{array}{c} \text{COUP} \\ | \\ \text{L} \\ | \\ \text{ETA} \end{array}$$

wherein:
COUP is a phenol, naphthol or pivalylacetanilide dye-forming coupler;
L is a divalent quinonemethide or an intramolecular nucleophilic displacement linking group; and ETA is a releasable 1-aryl-3-pyrazolidinone electron transfer agent bonded to the nitrogen atom in the 2-position thereof to L.

2. A photographic recording material comprising a support and a photosensitive silver halide emulsion layer which has, in reactive association therewith,
(a) an image dye-forming coupler compound,
(b) a compound capable of imagewise release of an electron transfer agent upon reaction with oxidized primary amine color developing agent, and
(c) a development inhibitor-releasing compound, wherein the compound capable of imagewise release of an electron transfer agent has the formula:

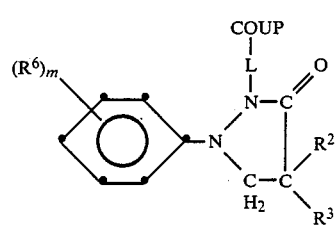

wherein:
COUP is a phenol, naphthol or pivalylacetanilide dye forming coupler;
L is a divalent linking group having one of the following formulae:

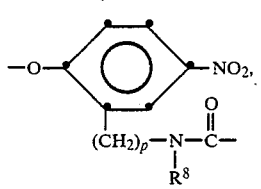

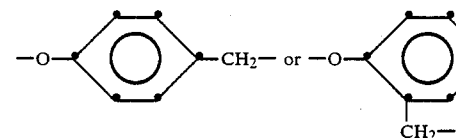

$R^2$ and $R^3$ are hydrogen or alkyl having from 1 to 3 carbon atoms or hydroxy methyl;
$R^6$ is hydrogen, methyl or methoxy;
$R^8$ is alkyl of from 1 to 3 carbon atoms; and
m and p are each 0 or 1.

3. A photographic recording material comprising a support and a photosensitive silver halide emulsion layer which has, in reactive association therewith,
(a) an image dye-forming coupler compound,
(b) a compound capable of imagewise release of an electron transfer agent upon reaction with oxidized primary amine color developing agent, and
(c) a development inhibitor-releasing compound, wherein the compound capable of imagewise release of an electron transfer agent has the formula:

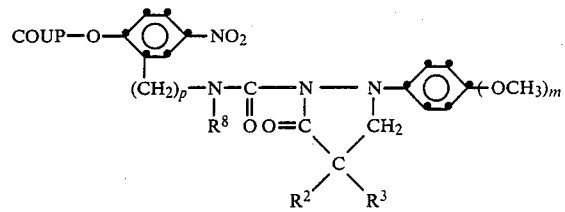

wherein:
COUP is a phenol, naphthol or pivalylacetanilide dye-forming coupler;
$R^2$ is hydrogen or methyl;
$R^3$ is hydroxymethyl or as defined for $R^2$;
$R^8$ is alkyl of from 1 to 3 carbons; and
m and p are 0 or .

4. A photographic recording material according to claim 1 wherein the compound capable of releasing the electron transfer agent has the structural formula:

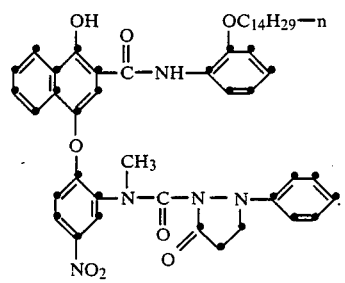

5. A photographic recording material according to claim 1 wherein the compound capable of releasing the electron transfer agent has the structural formula:

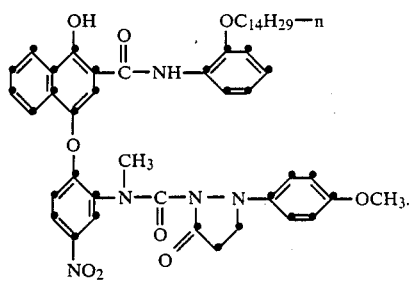

6. A photographic recording material according to claim 1 wherein the compound capable of releasing the electron transfer agent has the structural formula:

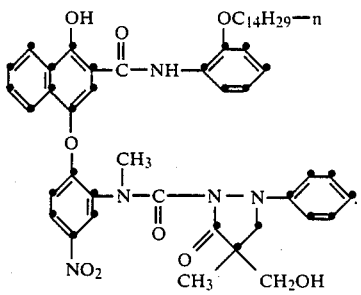

7. A photographic recording material according to claim 1 wherein the compound capable of releasing the electron transfer agent has the structural formula:
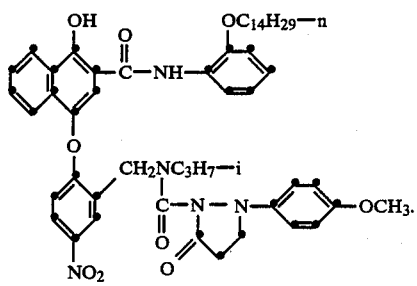
8. A photographic recording material according to claim 1 wherein the compound capable of releasing the electron transfer agent has the structural formula:
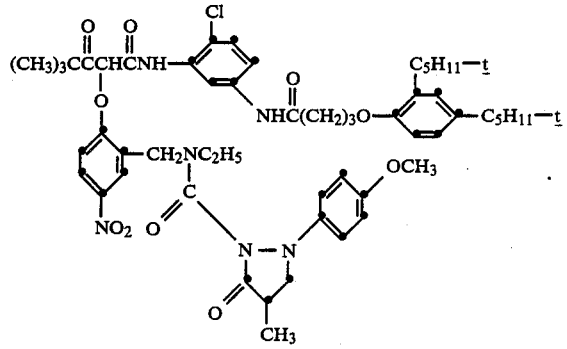
* * * * *

UNITED STATES PATENT AND TRADEMARK OFFICE
CERTIFICATE OF CORRECTION

PATENT NO. : 4,912,025
DATED : March 27, 1990
INVENTOR(S) : N. B. Platt et al.

It is certified that error appears in the above-identified patent and that said Letters Patent is hereby corrected as shown below.

Column 38, line 18, after "or" insert --1--.

Signed and Sealed this

Twenty-eighth Day of May, 1991

*Attest:*

HARRY F. MANBECK, JR.

*Attesting Officer*  *Commissioner of Patents and Trademarks*